United States Patent [19]

Hommeltoft

[11] Patent Number: 5,603,812
[45] Date of Patent: Feb. 18, 1997

[54] PROCESS FOR THE RECOVERY OF A STRONG ACID FROM AN AQUEOUS SOLUTION

[75] Inventor: Sven I. Hommeltoft, Hillerod, Denmark

[73] Assignee: Haldor Topsøe A/S, Copenhagen, Denmark

[21] Appl. No.: 301,842

[22] Filed: Sep. 7, 1994

[30] Foreign Application Priority Data

Jun. 17, 1994 [DK] Denmark .................................. 0707/94

[51] Int. Cl.$^6$ ..................................................... B01D 3/34
[52] U.S. Cl. .............................. 203/29; 203/49; 203/71; 203/85; 585/721
[58] Field of Search .................... 203/12, 14, 34, 203/49, 71, 85, 95, 29; 585/719, 721, 724, 725

[56] References Cited

U.S. PATENT DOCUMENTS 4,362,601  12/1982  Morita ....................................... 203/19
5,220,095   6/1993  Hommeltoft ............................. 585/720

Primary Examiner—Robert J. Warden
Assistant Examiner—Krisanne M. Thornton
Attorney, Agent, or Firm—Ostrolenk, Faber, Gerb & Soffen, LLP

[57] ABSTRACT

A process for the recovery of an acid in its anhydrous form from an aqueous solution containing the acid in its hydrated form. The process includes adding to the solution a weak base in the form of a soluble salt of the acid, and concentrating the solution containing the acid hydrate and the salt of the acid to a substantially water-free, acid-salt mixture. The acid is distilled off in its anhydrous form from the acid-salt mixture.

9 Claims, 1 Drawing Sheet

PROCESS FOR THE RECOVERY OF A STRONG ACID FROM AN AQUEOUS SOLUTION

BACKGROUND OF THE INVENTION

1. Field of the Invention

The present invention is related to the recovery of strong acids from an aqueous solution, and, in particular, to a process, wherein the acid is regained in its anhydrous form from water by a distillation process.

2. Description of the Related Art

Strong acids are employed in the chemical industry as useful catalysts in a large number of hydrocarbon conversion processes. As an example, hydrogen fluoride and sulfuric acids are used in large quantities in the alkylation of hydrocarbons to produce high quality gasoline. Use of perfluorinated sulfonic acids, as catalyst in the alkylation process, has recently been described in the literature.

In order to meet environmental requirements and to improve process economy in a process being catalyzed by a strong acid, it is desirable to recover and to reuse the acid from a process effluent stream containing recoverable quantities of spent acid.

Simple recovery methods would comprise extraction of spent acid into an aqueous phase and subsequent removal of water by distillation or evaporation.

Because of strong interactions between water and the acid, distillation of diluted aqueous solution of the acid, however, results in recovery of the acid in its hydrate form. Acid hydrates are catalytically inactive, and it is, therefore, necessary further to process recovered acid hydrate to its anhydrous form.

SUMMARY OF THE INVENTION

It has now been found that addition of a weak base to an aqueous solution of a strong acid provides recovery of the acid in its anhydrous form by a sequence of evaporation of water and subsequent recovery of the anhydrous acid by distillation.

As a theoretical explanation of these phenomena, the weak base interacts with acid protons and competes, thereby, with water molecules, leaving water more volatile than it would be solely in combination with the acid. After removal of water, it is possible to distil off the acid from the mixed base acid phase in its anhydrous form.

Pursuant to this finding, the present invention provides a process for the recovery of an acid in its anhydrous form from an aqueous solution containing the acid in its hydrated form, comprising the steps of adding to the solution a weak base in the form of a soluble salt of the acid;

evaporating water from the solution containing the acid hydrate and the salt of the acid to a substantially water free acid-salt mixture, and finally distilling off the acid in its anhydrous form from the mixture.

Based on the above theoretical explanation of the invention, proper bases for use in the process are selected from salts which interact with the acid hydrate.

Suitable bases include, pyridine, pyrrolidine and/or alkyl substituted pyridine and pyrrolidine, and cesium salts of the acid to be recovered, such as salts with trialkyl amine.

The invention is, as mentioned before, useful in the recovery of acids being catalytically active in the alkylation of a paraffinic hydrocarbon feedstock. Those processes conventionally employ hydrogen fluoride as alkylation catalyst. Alkylation process being catalyzed by a perfluorinated sulfonic acid is further known from U.S. Pat. No. 5,220,095. In the known alkylation processes considerable economic and environmental advantages are gained when recovering spent acid catalyst by simple extraction from an alkylation effluent stream with water and processing the aqueous extract in accordance with the above recovery process.

Accordingly, the invention further provides improvements in the alkylation of a hydrocarbon feedstock in the presence of an acid catalyst comprising the steps of extracting with water an alkylation effluent stream containing spent acid catalyst;

adding to the aqueous extract a salt of the acid catalyst;

concentrating the salt containing extract;

distilling off the acid from the concentrated extract; and recycling the acid to the alkylation process.

The steps of concentrating and distillating of the acid during the acid recovery process may be carried out conventionally by removing excess of water from the acid hydrate salt mixture at reduced pressure in an evaporation column and then cycling the mixture to a distillation column for recovery of the anhydrous acid. Remaining amounts of the acid salt mixture may then be recycled from the distillation column to the evaporation column.

Alternatively, the acid may be recovered in its anhydrous form in a continuous or flash distillation process by passing the solution of the acid salt mixture over a hot surface at a temperature or pressure, where water continuously evaporates from the mixture. In a subsequent step, the dehydrated mixture is passed over a further hot surface at higher temperature and/or lower pressure and the acid is continuously distilled off, while the base is recycled to the first step.

DETAILED DESCRIPTION OF THE PREFERRED EMBODIMENTS

Figure 1:
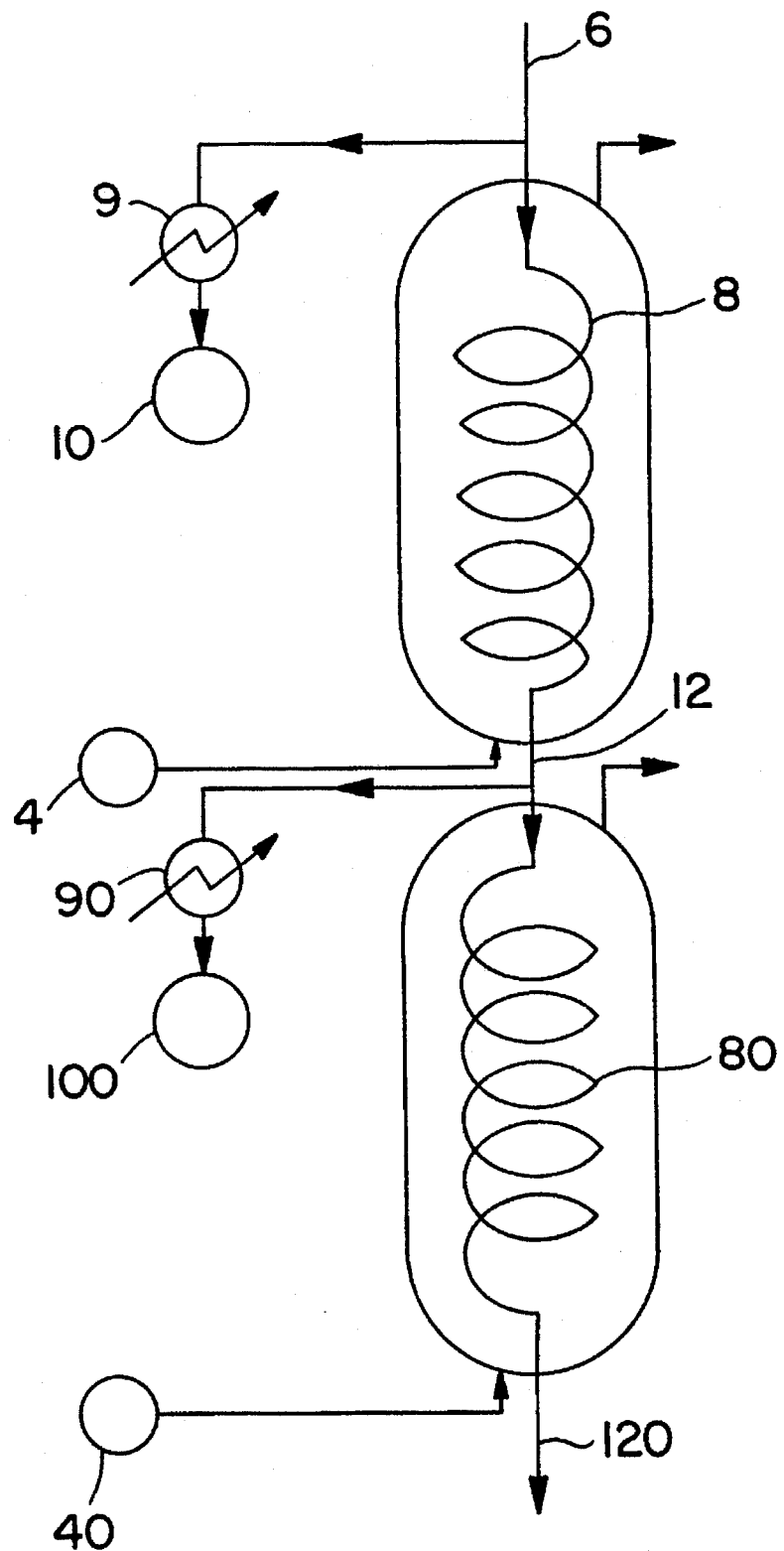
FIG. 1 is a schematic representation of an apparatus used in a distillation according to the present invention.

In the following Examples specific embodiments of the invention are described in detail.

EXAMPLE 1

150 g (1.00 mole) trifluoromethane sulfonic acid ($CF_3SO_3H$) were poured on ice to form an aqueous solution. To the solution 55.5 g (0.55 mole) triethyl amine were added and excess water evaporated at a temperature of 90° C., and a pressure of about 50 mbar. The evaporated solution contained 230 g of a salt/acid mixture with a content of water of 11.2%.

220 g of this mixture (equivalent to 0.53 mole triethyl ammonium triflate+0.43 mole $CF_3SO_3H$+1.37 mole water) were distilled from an oil bath at 1.5–2.0 mbar. The mixture started to boil at a bath temperature of 65° C. The distillate could not be condensed at room temperature, but was collected in a freezing trap at −196° C. 24.4 g water were collected in the freezing trap. At a bath temperature of 190°–220° C. a distillate, which initially condensed at 95° C. was collected. As a first fraction 7.68 g distillate consisting of $CF_3SO_3H$ containing 4% water (0.05 mole acid) were collected at a condensation temperature of 95°–90° C. The condensation temperature fell gradually to 44° C. and a second fraction of distillate consisting of 32.2 g substantially anhydrous acid containing 0.36% water (0.21 mole) $CF_3SO_3H$ was obtained. The residue of the distillation consisted of 154.2 g salt/acid mixture with less than 0.1% water.

EXAMPLE 2

21.2 g (0.10 mole) trimethyl ammonium triflate were mixed with 25.7 g (0.15 mole) $CF_3SO_3H \cdot H_2O$ (trifluoromethanesulfonic acid monohydrate) and distilled at 2 mbar from an oil bath. A pre-run of water (1.63 g, 0.09 mole) and two distillate fractions were collected as described in Example 1. The first fraction contained 15.84 g acid with a water content of 6.4% (0.056 mole water+0.10 mole trifluoromethanesulfonic acid). The second fraction consisted of 5.1 g acid containing less than 0.2% water (0.033 mole trifluoromethanesulfonic acid).

EXAMPLE 3

19.87 g (79 mmole) triethylammonium triflate were mixed with 10.34 g (62 mmole) trifluoromethanesulfonic acid hydrate and distilled at a pressure of 2 mbar from an oilbath. As the oilbath reached 90° C., the mixture boiled and the distillate did not condense at room temperature. The distillate was trapped in a freezing trap at −196° C. 1.03 g (57 mmole) water were found in the freezing trap.

At a bath temperature of 210°–222° C. 3.72 g distillate condensing at 42°–46° C. were collected. The distillate contained 3.72 g trifluoromethanesulfonic acid (24 mmole) with<0.1% water. Remaining in the distillation flask were 24.72 g acid/salt mixture containing 66.8% (111 mmole) triethylammonium triflate.

EXAMPLE 4

Distillation from tetraethylammonium triflate. To a flask containing 74.64 g (0.10 mole) 20% tetraethylammonium hydroxide ($Et_4N^+OH^-$) cooled in ice bath were added 37.62 g (0.25 mole) trifluoromethanesulfonic acid, resulting in an aqueous solution of 0.1 mole tetraethylammonium triflate and 0.15 mole of trifluoromethanesulfonic acid.

Most of the water was evaporated leaving 60.95 g of a mixture containing 15.9% (w/w) water.

57.05 g of the mixture were distilled as described above yielding 8.9 g of an aqueous pre-run containing 0.14 g trifluoromethanesulfonic acid and two distillate fractions. The first fraction consisted of 2.50 g trifluoromethanesulfonic acid with a water content of 3.3% and the second fraction consisted of 9.01 g trifluoromethanesulfonic acid with 0.84% water content.

EXAMPLE 5

Distillation of trifluoromethanesulfonic acid from methylpyrrolidine salt. A mixture of 44.53 g (0.297 mole) trifluoromethanesulfonic acid, 9.65 g (0.536 mole) water and 8.43 g (0.103 mole) methyl imidazole was distilled as described above. 7.6 g of an aqueous pre-run were obtained, which was collected in the freezing trap. 15.4 g of a first fraction containing trifluoromethanesulfonic acid with a water content 12.4% (w/w) corresponding to 13.5 g (0.09 mole) trifluoromethanesulfonic acid and a second fraction consisting of 10.0 g trifluoromethanesulfonic acid with a water content of 0.80% (w/w) (corresponding to 0.066 mole trifluoromethanesulfonic acid) were collected.

EXAMPLE 6

Distillation of pentafluorethanesulphonic acid from its triethylamine salt.

To 3.77 g (0.21 mole) water in 39.86 g (0.199 mole) $C_2F_5SO_3H$ were added 10.64 g (0.105 mole) triethyl amine resulting in a mixture of 0.105 mole $Et_3NH^+C_2F_5SO_3^-$, 0.094 mole $C_2F_5SO_3H$ and 0.21 mole water. This mixture was distilled as described above to 3.28 g aqueous pre-run (in freezing trap) and 13.47 g acid with a water content of 0.4%, corresponding to 0.067 mole $C_2F_5SO_3H$.

EXAMPLE 7

Distillation of trifluoromethanesulfonic acid from its cesium salt.

29.65 g trifluoromethanesulfonic acid were added to 33.05 g 50 % (w/w) CsOH (0.110 mole CsOH, 0.92 mole water) forming a partially crystallized mixture. The mixture was distilled under vacuum as described above and a fraction containing 5.84 g of acid with a water content of 6.4% (w/w) was collected.

EXAMPLE 8

Distillation of trifluormethanesulfonic acid from its pyridine salt.

To 4.4 g (0.24 mole) water in 30.33 g (0.20 mole) $CF_3SO_3H$ were added 9.6 g (0.121 mole) pyridine. The obtained mixture was distilled as described above and 6.76 g acid with a water content of 0.9% (corresponding to 0.045 mole trifluoromethanesulfonic acid) were recovered.

EXAMPLE 9

Recovery of trifluormethanesulfonic acid from acid soluble oil formed as a by-product in an isobutane alkylation process.

The trifluoromethanesulfonic acid in an ASO/acid mixture (approx. 60% (w/w) trifluoromethanesulfonic acid) formed as by-product in a trifluoromethanesulfonic acid catalyzed alkylation process, was extracted with water to yield an aqueous solution containing 24.4% (w/w) trifluoromethanesulfonic acid.

55.05 g of the aqueous trifluoromethanesulfonic acid solution (13.4 g, 0.090 mole) obtained by extraction of the acid soluble oil mixture withdrawn from an alkylation reactor were added to the pyridine salt remanence left from Example 8 (7.4% (w/w) or 2.2 g (0.015 moles) trifluoromethanesulfonic acid content). Distillation of the obtained mixture resulted in the recovery of a fraction containing 8.5 g trifluoromethanesulfonic acid with a water content of 0.9% (w/w).

EXAMPLE 10

Distillation of pentafluoroethanesulfonic acid from triethylammonium triflate.

A mixture of 18.78 g (0.094 mole) $C_2F_5SO_3H$, 26.20 g (0.104 mole) $Et_3NH^+CF_3SO_3^-$ and 4.09 g (0.227 mole) water was distilled as described above. 8.54 g product distillate were collected. The distillate contained 1.4% (w/w) water in a mixture of $C_2F_5SO_3H$ and $CF_3SO_3H$ in the weight ratio of 10:9.

EXAMPLE 11

Flash distillation.

In this Example, water was removed from an acid base mixture by flash distillation by passage of the mixture over a hot surface at conditions, where continuous evaporation of water is provided.

The outside of the heated surface in the form of a glass spiral was heated to 215° C. by condensing vapor of dodecane. The pressure inside the spiral was adjusted to 25 mbar.

A feed mixture containing 62% (w/w) triethylammonium triflate, 29% (w/w) trifluoromethanesulfonic acid and 9% (w/w) water were fed at a rate of 1.88 g/min. and the dehydrated acid mixture was collected in a collector at the outlet of the spiral. The mixture contained 0.21% (w/w) water and 25% trifluoromethanesulfonic acid. The remainder of the acid was found in the aqueous distillate in a product collector connected to the inlet of the spiral.

EXAMPLE 12

Acid recovery.

In a process similar to the process of Example 11, the outside of the heated surface of the glasspiral was heated to 215° C. by condensing vapor of dodecane and the pressure inside the spiral was adjusted to 1 mbar. A feed mixture containing 65% (w/w)-triethylammonium triflate, 35% (w/w) trifluoromethanesulfonic acid and 0.3% (w/w) water were fed at a rate of 1.97 g/min. and the acid was collected in the product collector at a rate of 0.5 g/min corresponding to 73% recovery.

EXAMPLE 13

Simultaneous water stripping and acid recovery. The equipment used for this Example is shown in FIG. 1. It consists of two distillation units connected in series. A first Unit 2 was used for water stripping, Unit 2 was heated with condensing n-decane (174° C.) from an evaporator 4—Unit 2 was kept under a pressure of 25–30 mbar. A second Unit 20 was used as acid recovery unit and was heated by condensing n-dodecane (216° C.) from an evaporator 40 and kept at a pressure of 2.5–3 mbar.

A feed mixture with the same composition as in Example 11 was fed from line 6 into the first unit at a rate of 1.8 g/min. In the first unit, the mixture passed through a glass spiral 8 being heated at the outside by condensing n-decane. By passage through spiral 8, water was stripped of the mixture and collected in water cooled 9 collector 10. The substantial water free mixture leaving spiral 8 through line 12 was then introduced into a glass spiral 80 in Unit 20. When passing through spiral 80, the acid in its dehydrated form was stripped of the acid salt mixture and collected in water cooled 90 acid collector 100 at a rate of 0.25 g/min. Residual acid salt mixture was withdrawn from Unit 20 through line 120 at the outlet of spiral 80.

EXAMPLE 14

Example 14 was carried out similar to Example 13, with the exception that the acid recovery Unit 20 was heated by condensing tetradecane (252° C.), whereas Unit 2 was heated by condensing decane (174° C.).

A feed mixture with the same composition as in Example 1 was fed to the first unit at a rate of 2.8 g/min., and the recovered acid collected in the acid collector of the second unit at a rate of 0.59 g/min. The water content of the recovered acid was 3.0% (w/w).

EXAMPLE 15

Regeneration of acid oil (ASO) from alkylation process.

The trifluoromethanesulfonic acid in an ASO/acid mixture (approx. 60% (w/w) trifluoromethanesulfonic acid) formed as by-product in a trifluoromethanesulfonic acid catalyzed alkylation process, was extracted with water to yield an aqueous solution containing 24.4% (w/w) trifluoromethanesulfonic acid.

112.2 g of this solution (27.4 g, 0.18 mole TfOH) were concentrated by boiling off 71.8 g of water at atmospheric pressure leaving the acid as 40.4 g concentrate (calculated acid content: 67.7% (w/w)). This concentrate was combined with a 71.4 g salt mixture (acid content: 6.7% (w/w)) from a previous acid recovery experiment performed as in Example 14.

In this acid recovery Example Unit 2 was heated by condensing undecane (196° C.), and Unit 20 was heated by condensing tetradecane (252° C.). The combined mixture was fed to the upper Unit 2 at a rate of 1.8 g/min., and an acid with a water content of 2.0% (w/w) was recovered at a rate of 0.4 g/min. The acid base mixture recovered contained 7.4% (w/w) trifluoromethanesulfonic acid.

I claim:

1. A process for the recovery of an acid in its anhydrous form, the process comprising the steps of:

providing an aqueous solution containing the acid in its hydrated form;

adding to the solution a weak base in the form of a soluble salt of the acid;

concentrating the solution containing the acid hydrate and the salt of the acid to a substantially water free acid-salt mixture; and distilling off the acid in its anhydrous form from the acid-salt mixture.

2. Process according to claim 1, wherein the soluble salt of the acid comprises a salt of the acid with trialkyl amine.

3. Process according to claim 2, wherein the trialkyl amine is trimethyl and/or triethyl amine.

4. Process according to claim 1, wherein the soluble salt of the acid comprises a salt of the acid with pyridine and/or alkyl-pyridine.

5. Process according to claim 1, wherein remaining amounts of the acid salt mixture in the distillation steps are recycled to the salt addition step.

6. Process according to claim 1, wherein the concentration of the solution containing the acid hydrate and the salt of the acid to a substantially water free acid-salt mixture is carried out continuously by passing the solution over a surface being maintained at elevated temperature and/or reduced pressure and continuously evaporating water from the solution.

7. Process according to claim 1, wherein the acid is distilled off in its anhydrous form from the acid-salt mixture continuously by passing the mixture over a surface being maintained at elevated temperature and/or reduced pressure.

8. A process for the alkylation of a hydrocarbon feedstock in the presence of an acid catalyst, the process comprising the steps of:

extracting with water an alkylation effluent stream containing spent acid catalyst;

adding to the aqueous extract a salt of the acid catalyst;

evaporating water from the salt-containing extract and obtaining a concentrated extract;

distilling off the acid from the concentrated extract; and recycling the acid to the alkylation process.

9. Process according to claim 8, comprising the additional step of concentrating the aqueous extract prior to adding the salt of the acid catalyst.

\* \* \* \* \*